United States Patent [19]

Heyman

[11] Patent Number: 4,869,722
[45] Date of Patent: Sep. 26, 1989

[54] FLOW MONITOR OF LIQUID DROPS

[75] Inventor: Joseph S. Heyman, Williamsburg, Va.

[73] Assignee: Measurement Resources Inc., Newport News, Va.

[21] Appl. No.: 146,289

[22] Filed: Jan. 20, 1988

[51] Int. Cl.⁴ ............................................. A61M 5/165
[52] U.S. Cl. ................................. 604/253; 73/861.21; 73/861.41; 604/65
[58] Field of Search ............ 128/DIG. 13; 73/861.21, 73/861.41; 604/65–67, 253

[56] References Cited

U.S. PATENT DOCUMENTS

| | | | |
|---|---|---|---|
| 2,807,012 | 9/1957 | Schwarz | 604/253 |
| 3,557,616 | 1/1971 | Landon, Jr. et al. | 340/611 |
| 3,832,998 | 9/1974 | Gregg | 604/253 |
| 3,871,229 | 3/1975 | Fletcher | 604/65 |
| 4,073,193 | 2/1978 | Mastandrea | 73/170 R |
| 4,105,028 | 8/1978 | Sadlier et al. | 604/253 |
| 4,135,395 | 1/1979 | Sullivan et al. | 73/861.21 |
| 4,328,801 | 5/1982 | Marx et al. | 604/65 |
| 4,432,761 | 2/1984 | Dawe | 604/253 |
| 4,583,975 | 4/1986 | Pekkarinen et al. | 604/253 |
| 4,674,337 | 6/1987 | Jonas | 73/861.21 |

FOREIGN PATENT DOCUMENTS 558155 12/1975 U.S.S.R. ........................... 73/861.41

Primary Examiner—C. Fred Rosenbaum
Assistant Examiner—Mario Costantino
Attorney, Agent, or Firm—William H. King

[57] ABSTRACT

A device for accurately monitoring the flow and flow rate of liquids that are released slowly so as to form drops. The drops fall from the tip of a drop funnel 13 onto a surface of liquid at the top of a reaction cell 16. Consequently, the height through which each drop falls is constant. The liquid volume of each drop is measured and the flow and flow rate are calculated by transducer 19 and flow meter processing electronics 22.

7 Claims, 1 Drawing Sheet

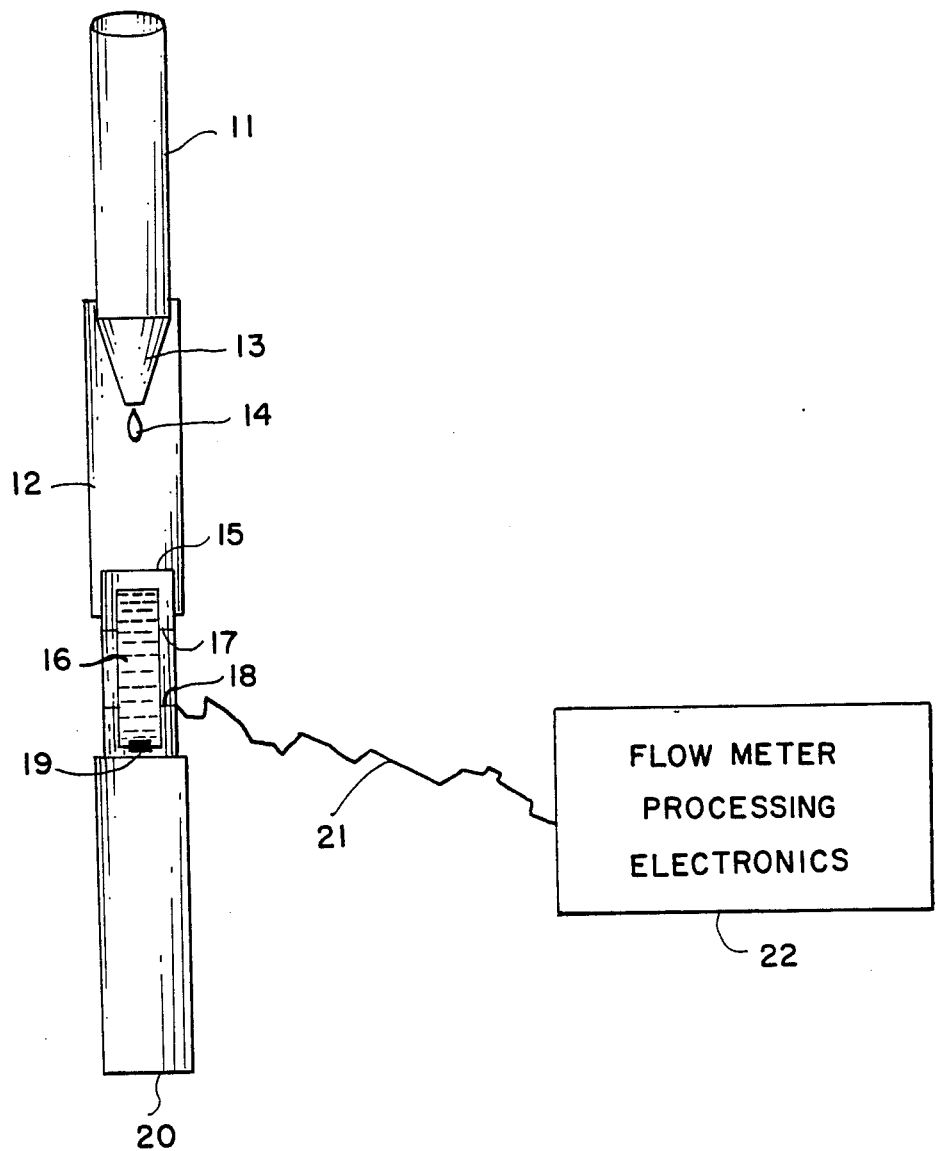

FLOW MONITOR OF LIQUID DROPS

BACKGROUND OF THE INVENTION

The invention relates generally to a flow meter and more specifically concerns accurately monitoring the flow rate of liquids that are released slowly so as to form drops. An example of a use for this invention is the medical use of intravenous liquids usually administered in a gravity feed system with flow control adjusted in a gravity feed system with flow control adjusted by clamping shut a plastic tube and monitoring the resulting drops.

Currently, the monitoring of liquids for intravenous applications is achieved by several means. First, and the most usual method, the drip rate is counted per unit time by watching the drops through a transport tube. The obvious disadvantages of this method are that it depends on the count accuracy of the attendant and is prone to human count error as well as error associated with the drop size variations. Determining the sizes of the drops is essential to accurately monitoring flow rate.

A second and more complex system involves a positive displacement pump which presses the liquid out of a tube using a roller. The flow is controlled by the tube diameter and the roller rotation rate. The positive displacement system is very expensive and must constrict the tube to function correctly. Therefore, the liquid must be able to sustain compressive crushing forces which may impair some liquids such as blood which contains physical cells.

A third group of systems included optical and electrical systems. Some of these systems only count the drops and are therefore subject to error. Some of these systems also measure the drop sizes. However, these systems are complex and subject to error in measuring the drop sizes.

An example of the third group of systems is disclosed in U.S. Pat. No. 4,583,975. In this system, the drops impinge on a surface of accumulated fluid and a piezoelectric element measures the sizes of the drops. Inasmuch as these measurements depend on the height through which the drops fall, it is essential to maintain this height constant at all times. That is the height of the surface of the accumulated fluid must be maintained at the same distance from where the drops are formed. This system does not provide a means for accurately maintaining this height constant and is therefore subject to error.

It is an object of the present invention to accurately monitor the flow rate of liquids that are released slowly so as to form drops.

Another object of this invention is to monitor the flow rate of liquids that are released slowly so as to form drops by accurately measuring the liquid volumes of the drops.

A further object of this invention is to monitor the flow rate of liquids that are released slowly so as to form drops by accurately maintaining a constant height through which the drops fall whereby the liquid volumes of the drops can be accurately measured.

Other objects and advantages of this invention will become apparent hereinafter in the specification and drawing.

SUMMARY OF THE INVENTION

The invention is apparatus for monitoring the flow rate of liquids that are released slowly so as to form drops. Conventional means are provided for producing drops that fall into a capture tube. A reaction cell is mounted inside the capture tube such that the drops fall into the reaction cell striking the surface of the liquid inside the reaction cell. Consequently, when the reaction cell is full there will be an overflow into the capture tube equal to the amount of liquid in each drop and all drops will have fallen through the same height. Means are provided for measuring the liquid volume of each drop that strikes the surface of the liquid in the reaction cell.

There is provided two different means for measuring the liquid volume of each drop. In one measuring means a transducer is attached to the reaction cell for measuring the acoustic pulses caused by the drop hitting the liquid surface at the top of the reaction cell. In the other measuring means the reaction cell is mounted inside the capture tube by isolator/damping rings thereby causing the entire capture cell to act as a dampled oscillator and a transducer acting as an accelerometer is attached to the reaction cell for measuring the damped oscillations.

BRIEF DESCRIPTION OF THE DRAWING

The FIGURE in this application is a schematic drawing of the invention.

DETAILED DESCRIPTION OF THE INVENTION

Turning now to the embodiment of the invention selected for illustration in the drawing the number 11 designates a tube through which a liquid is supplied from some source such as an intravenous bottle. Tube 11 extends into a drop funnel tube 12 and a drop funnel 13 is attached to the end of tube 11. The slow flow of liquid and surface tension causes a drop to form at the tip of drop funnel 13. Eventually a drop 14 is released from the drop funnel. The drop size depends on the diameter of the funnel, the surface tension of the liquid on the tube, as well as the liquid physical properties such as viscosity.

The drop falls into a capture tube 15 and strikes the surface of liquid contained in a reaction cell 16. Reaction cell 16 is mounted by isolator/damping rings 17 and 18 to the inside wall of capture tube 15. A transducer 19 attached to the bottom of reaction cell 16 produces a signal caused by the drop hitting the liquid surface that can be used to measure the liquid volume of the drop. Reaction cell 16 is open at the top allowing the cell to fill with the liquid such that the surface of the liquid is at the top of the cell. Hence the height through which the drop falls (from the tip of drop funnel 13 to the liquid surface at the top of reaction cell 16) is exactly the same for all drops. The delivered liquid (the drop) causes a displacement of liquid in the reaction cell and a quantity of liquid is caused to overflow and leave the reaction cell into a tube 20 which delivers the liquid to the user. The signal from the transducer 19 travels through a wire 21 and into a flow meter processing electronics 22. There, the signal is analyzed to determine the actual flow and flow rate and display that results for use by the monitor. The flow rate is the sum of the liquid volumes of drops and the flow rate is the flow per unit of time.

In a first embodiment of the measuring system transducer 19 measures the acoustic pulse caused by a drop hitting the liquid surface at the top of reaction cell 16. The energy contained in the drop is: $E = MGh$ where M is the mass of the drop, G is the acceleration of gravity, and h, the distance from the tip of drop funnel 13 to the liquid surface at the top of reaction cell 16, is the height through which the drop falls.

When the drop hits the liquid surface of the reaction cell, the energy carried by the drop is converted to a pressure wave (sound) in the liquid. The liquid volume of the drop is related to the integral of the pressure pulse measured by the transducer. The resulting electrical signal is processed by the flow meter processing electronic 22 in accordance with the equation $E=MGh$ to obtain the flow and flow rate.

Some liquids may have a viscosity or acoustic attenuation such that to measure their flow, it is more accurate to treat each drop as an impulse of momentum to the mass of the reaction cell. The mounting/isolator rings cause the entire reaction cell to act as a damped oscillator. For this case, a second embodiment of the measuring system is used. Instead of measuring the pressure pulse in the liquid itself, the vibration magnitude of the reaction cell as a unit mass is measured with transducer 19 acting as an accelerometer for the cell. The momentum, Pd of the drop is: $M_d V = P_d$, where V is the drop velocity which is found by $V=(2\ hG)^{0.5}$. The momentum acquired by the cell in capturing the drop is approximately equal to the $P_d$ (assuming the drop dynamics are fast compared to the cell natural frequency). Thus, $P_c = P_d = M_d(2hG)^{0.5} = M_c V_c$ where the subscript "c" refers to the cell. The maximum amplitude, X, of the cell vibration can be found knowing the effective spring constant, k, which holds the cell to the tube wall. Conservation of energy dictates that: $kX^2 = M_c(V_c)^2$ or $X = M_d(2\ Gh/kM_c)^{0.5}$. Therefore one can measure the mass of the drop knowing the amplitude of the cell vibration (measured) and the other constants, h, k, and $M_c$. The signal from transducer 19 is processed by flow meter processing electronics 22 in accordance with the above equations. This embodiment is especially appropriate for high viscosity liquids.

The advantage of this invention is that it provides a simple, inexpensive device for accurately monitoring the flow and flow rate of liquids that are released slowly so as to form drops. The accuracy of the device is accomplished by providing means that ensure that all drops fall through the same constant height.

Modifications and variations of the present invention can be made in light of the above teachings. For example, different means could be used to measure the liquid volumes of the drops.

What is claimed is:

1. Apparatus for monitoring the flow rate of liquids that are released slowly so as to form drops comprising:
   means for producing drops of a liquid;
   capture tube means located beneath said means for producing drops for receiving said produced drops;
   reaction cell means with an open top and having walls defining a finite volume mounted inside said capture tube means such that said drops fall through said open top into the finite volume of said reaction cell means and such that any overflow will flow into said capture tube means; and
   means for measuring the sum of the liquid volume of the drops that strike the surface of the liquid said reaction means;
   whereby whenever the reaction cell means is full of said liquid there will be overflow of the liquid into the capture tube means exactly equal to the amount of liquid in the drops and each drop will fall through a precise height h thereby allowing the said means for measuring to make exact measurements.

2. Apparatus according to claim 1 wherein said means for measuring includes a transducer means attached to said reaction cell means for measuring the acoustic pulses caused by the drops hitting the liquid surface at the top of the reaction cell means.

3. Apparatus according to claim 2 where said transducer means is attached to the end of said reaction cell opposite the open top of said reaction cell means.

4. Apparatus according to claim 2 wherein said measuring means includes means for measuring the liquid volume of the drops in accordance with the formula $E=MGh$ where M is the measurement of a drop, G is the acceleration of gravity, h is the height through which the drop falls and E is the transducer measurement.

5. Apparatus according to claim 1 wherein said reaction cell means is mounted inside said capture tube means by isolator/damping rings thereby causing the entire capture cell means to act as a damped oscillator and wherein said measuring means includes a transducer means attached to said reaction cell means and acting as an accelerometer for the reaction cell means.

6. Apparatus according to claim 5 wherein said means for measuring includes a flow meter processing electronic means connected to said transducer means for measuring the liquid volume of the drops in accordance with the formulas $M_d V = P_d$, $V=(2\ hG)^{0.5}$, $P_c = P_d = M_d(2\ hG)^{0.5} = M_c V_c$ and $kX^2 = M_c(V_c)^2$ or $X = M_d(2\ Gh/kM_c)^{0.5}$ where $P_d$ is drop momentum, V is drop velocity, the subscript "c" refers to reaction cell, X is the maximum amplitude of the reaction cell vibration, k is the effective spring constant, and h is the height through which the drops fall.

7. A method for monitoring the flow rate of a liquid that is released slowly so as to form drops comprising the steps of:
   collecting an exact finite volume of said liquid;
   locating said volume such that said drops will fall onto the upper surface of said volume of liquid causing overflows of said volume of liquid in a reaction cell having walls defining a finite volume thereby maintaining said upper surface at an exact location such that all said drops will fall through an equal height;
   collecting said overflows of said volume of liquid; and
   measuring the liquid volumes of the drops falling onto the upper surface of said volume of liquid.

* * * * *